(12) United States Patent
Bienhaus et al.

(10) Patent No.: US 6,919,175 B1
(45) Date of Patent: Jul. 19, 2005

(54) SYSTEM FOR RELEASING AND ISOLATING NUCLEIC ACIDS

(75) Inventors: Gerhard Bienhaus, Wielenbach (DE); Ulrich Schubert, Starnberg (DE); Uwe Kolb, Weilheim (DE); Burkhard Stolz, Huglfing (DE); Manfred Pasch, Tutzing (DE)

(73) Assignee: Roche Diagnostics GmbH, Penzberg (DE)

( * ) Notice: Subject to any disclaimer, the term of this patent is extended or adjusted under 35 U.S.C. 154(b) by 0 days.

(21) Appl. No.: 09/558,038

(22) Filed: Apr. 26, 2000

Related U.S. Application Data

(62) Division of application No. 08/930,247, filed as application No. PCT/EP96/01368 on Mar. 28, 1996.

(30) Foreign Application Priority Data

Apr. 1, 1995 (DE) .......................................... 195 12 368

(51) Int. Cl.[7] .......................... C12Q 1/68; C12N 15/00; C12N 15/63; C12N 1/20; C07H 21/04
(52) U.S. Cl. ..................... 435/6; 435/320.1; 435/252.8; 435/174; 435/183; 382/129; 382/133; 382/153; 382/173; 382/286; 382/291; 702/19; 702/22; 935/10; 935/24; 935/72; 536/22.1
(58) Field of Search .......................... 435/6, 91.1, 91.2, 435/270, 262, 267; 536/24.3; 935/6; 436/518, 21

(56) References Cited

U.S. PATENT DOCUMENTS

| | | | |
|---|---|---|---|
| 5,466,574 A | | 11/1995 | Liberti et al. |
| 5,498,550 A | | 3/1996 | Fujiwara et al. |
| 5,508,164 A | | 4/1996 | Kausch et al. |
| 5,523,231 A | * | 6/1996 | Reeve |
| 5,536,475 A | | 7/1996 | Moubayed et al. |
| 5,558,839 A | | 9/1996 | Matte et al. |
| 5,702,950 A | | 12/1997 | Tajima |
| 5,705,062 A | | 1/1998 | Knobel |
| 5,910,446 A | * | 6/1999 | Ansfield ....................... 436/21 |

FOREIGN PATENT DOCUMENTS

| | | |
|---|---|---|
| EP | 0 265 244 A2 | 4/1988 |
| EP | 0 389 063 A2 | 9/1990 |
| EP | 0 687 502 A2 | 12/1995 |
| JP | 4-349692 | 12/1992 |
| WO | WO 91/15768 | 10/1991 |
| WO | WO 92/05443 | 4/1992 |
| WO | WO 93/25912 | 12/1993 |
| WO | WO 94/20858 | 9/1994 |

\* cited by examiner

*Primary Examiner*—Jeffrey Fredman
*Assistant Examiner*—Arun Chakrabarti
(74) *Attorney, Agent, or Firm*—Arent Fox

(57) ABSTRACT

A procedure for the release and isolation of nucleic acids from biological compartments of a sample always uses an instrument that can hold one or more sample processsing vessels, maintain the sample processing vessels at a constant temperature, shake the sample processing vessels and separate magnetic particles by means of magnetic force. This system greatly simplifies the isolation of nucleic acids.

24 Claims, 8 Drawing Sheets

SYSTEM FOR RELEASING AND ISOLATING NUCLEIC ACIDS

This is a divisional of application Ser. No. 08/930,247, filed Feb. 17, 1998, which is a 371 of PCT application Ser. No. PCT/EP96/01368, filed Mar. 28, 1996.

The object of the invention is a system for the release and isolation of nucleic acids and a procedure for using this system.

Detection procedures based on the determination of nucleic acids in a sample have increased in significance recently. This is due, among other things, to the high sensitivity of detection that these procedures can achieve. In terms of sensitivity, nucleic acid detection procedures are basically superior to antigen detection procedures. Although antigens are often relatively accessible in a sample, numerous steps are usually required to make nucleic acids accessible, especially when detecting organisms. In addition, nucleic acids are usually present in very low concentrations. Purification procedures for isolating nudeic acids from samples containing cells are known in particular, although they require a great deal of time and effort.

The sensitivity of the sample enrichment and pretreatment systems for nucleic acids currently on the market is often insufficient. In addition, automated sample pretreatment systems are not sufficiently safe from contamination to enable amplification e.g. using the PCR. Another disadvantage of the automated sample pretreatment systems currently available is that they require the use of organic solvents (phenol and/or chloroform alcohol mixtures) to extract the nucleic acids.

The procedures in use today that immobilize nucleic acids basically use two principles to isolate nucleic acids. One principle calls for liquid samples containing nucleic acids to be aspirated through a solid phase which retains the nucleic acids. This step is preceded by a lysis step performed in a separate container. The nucleic acids are then dissolved from the solid matrix by aspirating an elution fluid through the matrix. The elution solution containing the nucleic acids is aspirated into a container for the next steps. It has been demonstrated, however, that the purity of the devices in use today does not meet the requirements for a subsequent amplification reaction, such as the PCR.

According to the second principle of nucleic acid isolation, the nucleic acids are removed by way of precipitation and then separated in a centrifuge. This procedure cannot be performed in a "batch" mode, however. Rather, it first requires that a solution containing cells be treated with lysing agents in a reaction vessel. The reaction mixture is then transferred by pipette from the container to a centrifugation tube. This tube contains an insert to which the released nucleic acids can adsorb, while the remaining fluid can flow to the bottom of the tube during centrifugation. The insert is treated one or more times with a fluid to wash the absorbed nudeic acids. For this step, the insert is transferred to a second centrifugation tube so that residues from the sample fluid do not reenter the insert. In the final step, the insert is placed in yet another container. An elution solution is then centrifuged through the insert to transfer the nucleic acids to another vessel that contains a solution that is capable of being processed further. This procedure is very susceptible to contamination, however, and requires transferring solutions between numerous reaction vessels.

The task of this invention was to provide a system for which the disadvantages of the state of the art are eliminated either completely or at least partially. In particular, this system can be used to absorb and desorb nucleic acids to a solid phase matrix without requiring a centrifuge for these steps.

A main feature of the invention is a receptacle for a sample processing vessel that can be kept at a constant temperature and set into motion in order to thoroughly mix the substances contained in the sample processing vessel. In addition, this receptacle is connected to a vacuum-generating system (e.g. a hose pump or a piston pump). The receptacle also makes it possible to separate magnetic particles within the sample processing vessel. Important advantages of the invention are the protection it provides against contamination (between samples and between the system and the environment), and its potential to hold enough sample processing vessels to ensure cost effectiveness.

This invention also provides a procedure for releasing and isolating or detecting nucleic acids from biological compartments of a sample with the following steps:

The sample is incubated in a sample processing vessel with magnetic particles that can bind with the biological compartments while the sample processing vessel is shaken, A magnet is positioned near the sample processing vessel in order to hold the magnetic particles against the wall of the vessel, The remaining fluid is removed from the sample processing vessel, The magnetic particles are resuspended in a second fluid by
a) removing the magnet away from the sample processing vessel so that the magnetic particles are no longer held against the wall of the vessel, while
b) shaking the sample processing vessel, The biological compartments are warmed and lysed, The lysis mixture is cooled under conditions that make it possible to immobilize or hybridize the nucleic acids to be isolated or detected.

This invention also provides a procedure for the release and isolation of nucleic acids from a suspension of biological compartments using magnetic particles with the following steps:

A sample is incubated in a sample processing vessel with magnetic particles in order to lyse the biological compartments, The lysis mixture is cooled and the nucleic acids to be isolated or detected are immobilized on the magnetic particles, The state of immobilization is eliminated and the nucleic acids to be isolated and purified are transferred to a vessel from which they can be pipetted.

Figure 1:
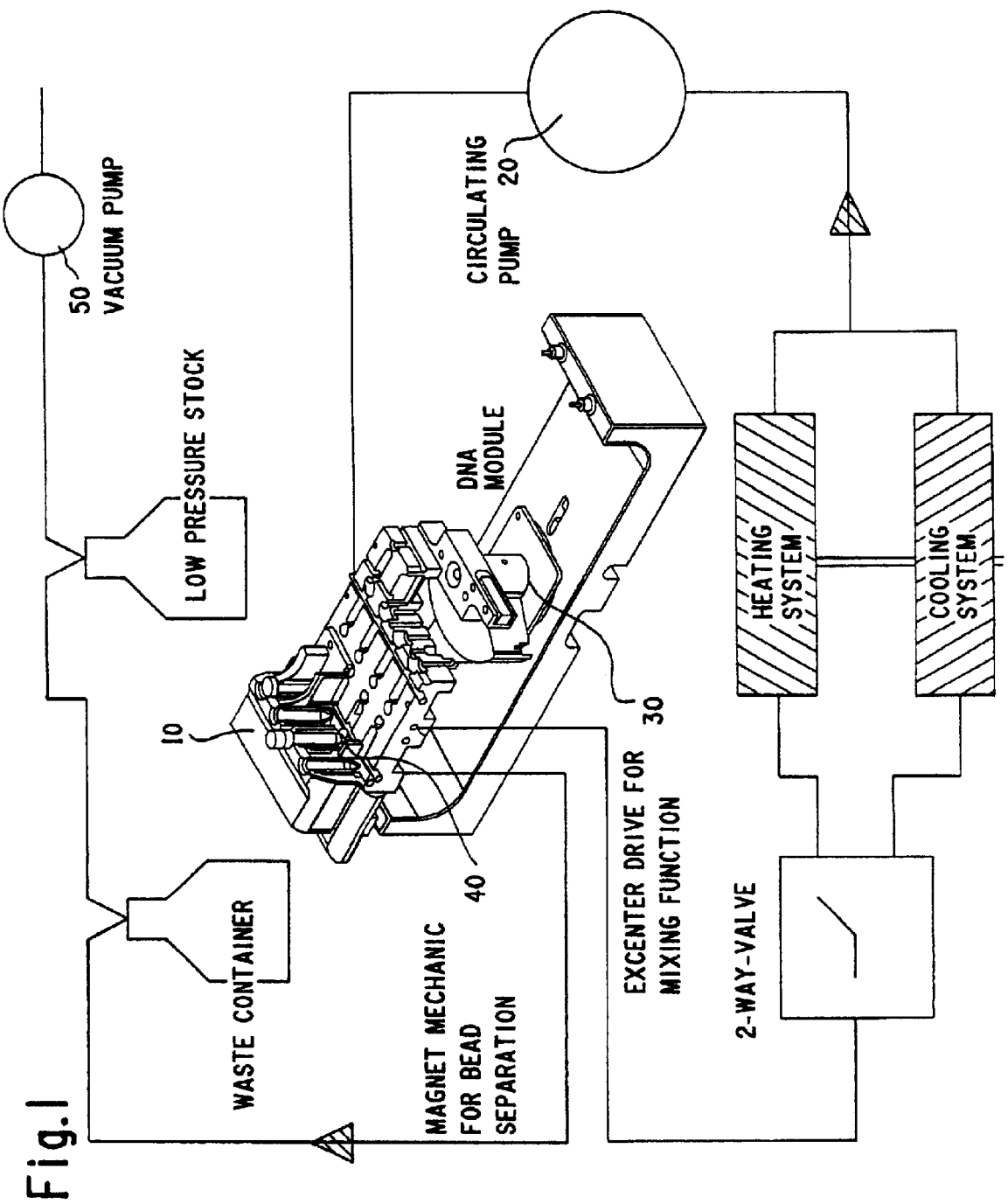
FIGS. 1 and 2 show a system for the release and/or isolation of nucleic acids in accordance with the invention.

"Nucleic acids" as described in context with this invention refer to nucleic raacids that are present in biological compartments. "Biological compartments" refer in particular to viruses or cells of bacterial origin especially preferred construction, the cells are basically present in a format in which they are basically separate from each other. In principle, however, this invention can also process multicellular compartments. These compartments and their nucleic acids are contained in a sample at the beginning of the procedure described by this invention. This sample is preferably a suspension of biological compartments in a fluid. These fluids can be obtained from bodily fluids such as blood, saliva or urine, for instance.

"Release of nucleic acids" as described in context with this invention refers to the discharge of nucleic acids from the biological compartments. Any means can be used to discharge the nucleic acids from the biological compartments. Preferably, the wall separating the biological compartments from the fluid is destroyed. This can be accomplished, for instance, by treating the compartments with cell wall destroying agents such as proteinase K.

"Isolation of nucleic acids" as described in context with this invention refers to the separation of nucleic acids from other components in the sample. "Other components in the sample" can include the walls of the biological compartments, their degradation products, other contents of the biological compartments and components of the fluid that surrounds the biological compartments in the sample. These components can include proteins or enzyme inhibitors, especially enzymes that degrade nucleic acids, such as Dnase or RNase. In this sense, isolation can also refer to a method for purifying nucleic acids. This isolation step can be specific or non-specific for other nucleic acids contained in the sample.

"Detection of nucleic acids" as described in context with this invention refers to a procedure in which the presence or quantity of nucleic acids is determined. These procedures can be performed quantitatively or qualitatively. The quantitative detection procedure usually requires that a comparison test be performed with a sample that-contains a known quantity of the nucleic acids to be detected. The detection can be sequence-specific or sequence non-specific. To make the detection specific, one usually uses "probes" that are characterized by the fact that they have a nucleobase sequence that is more or less characteristic for the nucleic acids in the sample. If the goal is to perform specific detection of nucleic acids, a probe is used that contains a base sequence that is complementary to the base sequence of the nucleic acids to be detected, but not, however, to other nucleic acids in the sample. Probes can be molecules that contain a group that can be detected either directly or indirectly. Groups that can be detected directly include radioactive ($^{32}P$), colored or fluorescent groups or metal atoms. Groups that can be detected indirectly include, for instance, compounds with an immunological or enzymatic effect such as antibodies, antigens, haptens, enzymes or enzymatically active sub-enzymes. These groups are detected in a subsequent reaction or sequence of reactions. Especially preferred are haptens, such as digoxigenin or biotin. Hapten-labelled probes of this nature can then be detected easily in a reaction with a labelled antibody against the hapten.

Description of the System

The object of the invention is a system for the release and/or isolation of nudeic acids from a suspension of biological compartments comprising the following components:

a receptacle (10) for one or more sample processing vessels (A), a thermostat unit (20) to maintain the sample processing vessels (A) and the fluids they contain at a constant temperature, a mechanical shaker (30) to shake the sample processing vessels (A), a separation device (40) to separate magnetic particles from fluid using magnetic force and deposit them on a wall of each sample processing vessel (A), and a pump unit (50) to remove fluid from the sample processing vessel (A).

The surface of the system is easy to clean and protects the operator from burns (e.g. by virtue of a plastic housing).

Figure 2:
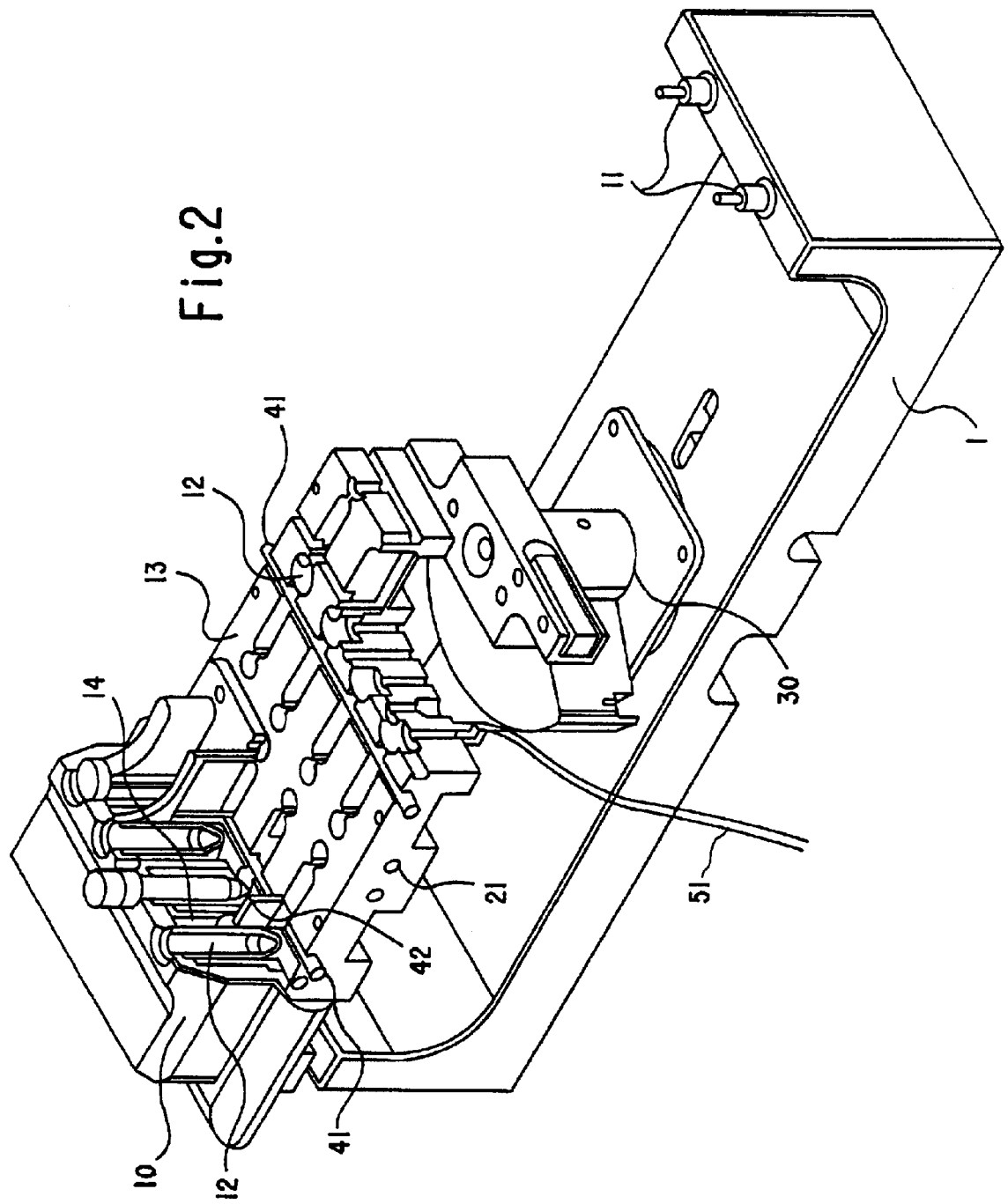

Drawings of a system comprising the units described by this invention are shown in FIGS. 1 and 2.

The system has a receptacle (10) for holding the sample processing vessels. This receptacle contains numerous recesses (12) or "cavities" into which the sample vessels are placed. The cavities are preferably arranged in a linear format or in sub-groups that are arranged in a linear format yet are at right angles to each other. The distance between the cavities is preferably the same distance that separates the wells of a microtiter plate and, more preferably, twice this distance. The cavities are designed to hold the sample vessels.

The sample processing vessel (A) can basically have any shape or design For instance, these sample processing vessels can be the wells of a microtiter plate (e.g. a 96-well format). The vessels are preferably cylindrical, however, with an opening at the top to receive fluid and, most preferably, an opening at the bottom from which fluid can exit (A 11). A sample processing vessel with this design can be used to reduce contamination while processing samples containing nucleic acids. These vessels are usually made of a plastic such as polypropylene.

In an especially preferred construction of this invention, vessels can be used that are described in the German design patent applications numbered 29505652.5 and 29505707.6.

The fluid in the sample processing vessels is kept at a constant temperature in the system described by this invention by means of a thermostat unit (20). This unit, which basically consists of components common to thermostats, is preferably integrated—at least partially—in the receptacle (10) in which the sample processing vessels can be placed. The receptacle (10) especially includes a metal block with good thermal conductivity. The shape of this metal block is designed to fit with the outer contour of the sample processing vessels in such a way that the walls of the sample processing vessels placed in the receptacle fit within the metal block as snugly as possible, so that heat can be transferred efficiently. The temperature in the block is increased or decreased, depending on the reaction to be performed in the sample processing vessel. The temperature can range from 4° C. to 95° C. Ideally, numerous electrical heating elements located as closely as possible to the sample processing vessel are used to increase the temperature. The fluid in the sample processing vessel is cooled by means of peltier elements that are also located as close to the sample processing vessels as possible. The temperature is regulated preferably by means of a fuzzy regulator or a PIDT regulator. A sufficient number of heat sensors are situated in proper locations within the thermostat unit.

Another construction of the thermostat unit (20) includes a block through which fluid flows. Fluids—usually water or aqueous saline solutions—are used as the incubation medium. Preferably, the incubation fluid is fed directly into openings (21) in the block (10) by means of a circulating pump via flexible tubes connected to a heating or cooling system. The volume of the incubation reservoir (represented in FIG. 1 with "heating unit" and "cooling unit") outside the DNA module is much larger than the dead volume of the DNA module in order to minimize this disturbance variable when the 2-way valve is switched over. The heating and cooling units maintain the fluid at a constant temperature before the process begins and can be programmed to operate at certain intervals if necessary. A regulator controls the valve and heating and cooling units, and, coupled with the appropriate volume flow achieved by the circulating pump, maintains the heating and cooling rates desired. The "thermostat unit"(20) in this construction refers to a combination of a block, circulating pump, heating unit, cooling unit and 2-way valve through which fluid flows. The "DNA module" refers to the device that includes the receptacle for the sample processing vessel, the shaking device and the separation device.

The system enables one to work with magnetic particles (beads). The term "magnetic particles" refers to particles that can be transported in a certain direction by means of magnetic force. These particles can be made of ferromagnetic or superparamagnetic materials, for instance. Especially preferred in the context of this invention are ferromagnetic materials. Particles are solid materials with a small diameter. Within the context of this invention, particles with an average particle size of more than 2.8 $\mu$m but less than 200 $\mu$m are especially suitable. Most preferably they have an average particle size of between 10 and 15 $\mu$m. The distribution of particle size is preferably homogenous. The surface of these particles is modified in such a way that they can bind with the biological compartments. Magnetic particles that are suitable for this application are the known and commercially available latex magnetic particles to which antibodies can be bound, for instance. Antibodies targeted against surface antigens of the biological compartments are used in particular to bind the biological compartments to the magnetic particles. Magnetic particles of this nature are also commercially available.

Glass-magnetic pigments with surfaces to which nucleic acids can bind can also be used. Glass-magnetic pigments of this nature are known from the German patent application number 19537985.3.

For the procedure described by this invention to be performed successfully, the magnetic particles must be bound to the inner wall of the sample processing vessel for certain reaction steps and then brought back into suspension in a subsequent step. In an especially preferred construction of this invention, a separation device (40) to which one or more permanent magnets or electromagnets are attached is moved towards the sample processing vessel in order to position the magnets. The removal of the magnet away from the sample processing container—which is necessary for separation to be performed efficiently—depends to a large extent on the strength of the magnetic field that the magnets can produce, the size of the magnetic particles, and on the ability of the magnetic particles to be magnetized. The nature of the subsequent processing steps (e.g. mechanical stressing of the magnets) also determines the strength of the magnetic field to be used. If a permanent magnet is used, it is moved from a position where it cannot separate the magnetic particles and into the vicinity of the vessel so that the magnetic particles are held against the vessel wall. If an electromagnetic is used, it is turned on and allowed to remain in the power ON state until the biological compartments held against the vessel wall are processed.

"Positioning a magnet in the vicinity of the vessel" also refers to the case in which the vessel is brought into the vicinity of the magnet Ultimately, it refers merely to the motion of the magnet in relation to the vessel.

The separation device (40) preferably has a magnet that can be moved towards the sample processing vessel along a predetermined path, e.g. on rails or, preferably, by moving the magnet on a circular track, e.g. along an axis that passes next to the sample vessel The separation unit also comprises a motor that can drive the movement of the magnet towards and away from the sample processing vessel.

In another construction, the separation unit (40) has a gear rack that can be driven in linear fashion by means of a d.c. motor or a stepping motor. A device that holds the magnets—permanent magnets in this case—is positioned at a right angle to the gear rack light barriers can be used to detect the end positions of the movement of the magnets. In the preferred construction, one magnet is assigned to each sample processing vessel, the front face of which is moved into position next to the vessel. Two magnets can also be moved into position next to each sample processing vessel, however. Preferably, one magnet is moved into position next to 2 vessels, so that only n+1 magnets are required for n vessels.

For the separation step, the magnets must be moved as close to the sample processing vessels as possible in order to achieve a high rate of separation of the magnetic particles. It is also important that the distance traveled by the magnets between the positions be sufficiently long. Depending on the material and geometry of the magnet used, the magnets must be up to 40 mm away from the sample processing vessel to prevent unintentional separation of the magnetic particles in the sample processing vessel. For the instrument to function properly, it is important that the magnetic forces only affect the particles in the sample processing vessel, if this is so desired. To achieve this effect, the inactive position of the magnet must be far enough away from the vessel that the magnetic field has no effect on the movement of the particles.

This effect can also be achieved in such a way that the distance between the magnet and the sample processing vessel is not changed. The magnetic fields can simply be interrupted by a $\mu$-metal that is moved into a location between the vessel and the magnet.

In another possible construction, the magnets are arranged on a rotatable shaft driven by a d.c. motor. This construction enables the magnets to be moved along a circular path. The magnets themselves can be arranged on this shaft in any order that moves them towards or away from the sample processing vessels. In addition, a drive mechanism is preferred in which one shaft with a number of magnets is situated on each opposing side of the system. The shafts are driven by a motor by means of a gear rack. With this arrangement, every two magnets move in a synchronous motion towards the front face of the sample processing vessel.

Magnets for the invention described here preferably have a mass of between 0.5 and 5 g, and, especially preferred, between 1 and 4 g. The outer dimensions of the prototype are 10 mm×10 mm×3 mm. Materials that have been proven to be suitable for a permanent magnet are rare earth materials (e.g. NeFeB, VACODYM 370 HR) with an optimal BH maximum at the smallest dimensions. For the separation step to proceed efficiently, it is advantageous to design the gradients of the magnetic field to be especially pronounced. For this reason, the magnets should be located as close to the vessel as possible. The sample processing vessels are preferably made of materials that weaken the magnetic field as little as possible, such as polypropylene.

Tubes (51) that are connected to a vacuum-generating system are attached to the underside of the cavity on the unit that holds the sample processing vessels. One tube is assigned to each cavity. Since there are openings in the bottom of the sample processing vessels, a vacuum can be created to aspirate the contents of the sample processing vessels and deposit them in the waste container. In the construction shown in FIG. 2, each cavity has a seal that prevents air from being introduced into the space between the sample processing vessel and the inlet (14) when the waste material is aspirated.

The vacuum system basically comprises a piston pump (50) that is connected with the cavities via a tubing system. A waste container into which the fluid is deposited is located between the piston pump and the cavities. The fluid that is aspirated out of the sample processing vessels is waste. In addition, a valve is situated between every sample processing vessel and the waste container. This valve enables the vacuum to be switched to each cavity when the system is permanently evacuated from the pump, past the waste container, and up to the valve. With the construction provided by the invention, the sample processing vessels can be aspirated in parallel and sequentially.

In another construction, piston pumps and valves are replaced with a flow inducer. The waste container is not evacuated permanently in this case, rather, it is situated in the fluid stream behind the cavities and the flow inducer. With this arrangement, the cavities can only be aspirated in parallel. Numerous flow inducers may be used as well, which then serve a certain number of cavities and enable work to be performed in a partially sequential fashion.

The sample processing vessels are preferably moved in a horizontal direction. In an especially preferred construction, the receptacle (10)—which contains recesses (12) that hold one sample vessel each—is moved, so that all sample vessels in the system are shaken. Vibration absorbers (11) serve to reduce the amount of movement transferred to the rest of the instrument This invention preferably uses a mechanical shaker (30) that moves the sample processing vessels (A). This unit can basically be any mechanical device that is suitable for mixing fluids in a vessel. A preferred example of such a unit is described below.

A stepping motor with an eccentric cam and an equalizing weight situated on a fixed framework (1) move the receptacle—which is placed on vibration absorbers on this framework—in a circular, eccentric path with a fixed amplitude and a variable frequency. The preferred amplitude A is $\leq 1.5$ mm, and the preferred frequency (f) is greater than 1 Hz and less than 50 Hz. The mixing and resuspension step lasts between 5 and 30 s, depending on the physical characteristics of the sample material. The amplitude can be varied by replacing the eccentric cam.

Combining the system provided by this invention with an automated pipetting system is not a logical step, because this would require that the sample vessels be placed in a definite position before and during the pipetting steps. If the sample vessels are not placed in a definite position, they are located in a different position after the shaking step. If the position of the vessels during the pipetting step is not specified exactly, it may not be possible to perform the pipetting procedure correctly. For this reason, the instrument ensures that the vessel is located in a defined "home" position after the shaking procedure, from where a pipetting step or other processes can be performed.

It is advantageous to use a stepping motor instead of a d.c, motor in order to ensure a defined home position. In a preferred construction, the home position is detected with a light barrier.

The instrument may also be designed to be non-invasive, as described below. However, these alternatives are more complex in design (Versions 1 and 2), or they utilize mixing steps (3) that take a longer time to complete:

1. A combination of one, two or three linear drives for the receptacle on the plane or in a space (X, Y and Z-axis) to create Lissajous curves, for instance.
2. Wobbling by tilting the framework (1) at a certain angle and placing the receptacle (10) at the opposite end.
3. Magnetic stirrig mechanism
4. Swirling or tapping the DNA module.

The system components are coupled in such a way as to be functional, e.g. via integration of the magnets in the unit (10). The system components are also coupled chronologically. For instance, the units are operated in the sequence required for the application desired, e.g. via a computer program or by the operator initiating the steps individually.

Description of the Procedure

Version A

In the initial step, the sample is incubated in a sample processing vessel with magnetic particles (beads) that can bind with the biological compartments while the sample processing vessel is shaken.

The incubation of the samples with the magnetic particles can take place in any fashion. It is necessary for the sample and the magnetic particles to be placed in the sample processing vessel. Neither the method by which the sample and magnetic particles are placed in the vessel nor the sequence in which this takes place is especially significant for the procedure provided by this invention. Preferably, however, the magnetic particles are pipetted into the sample processing vessel in a suspension with a known concentration of magnetic particles. The sample is pipetted into the sample processing vessel either before or after the suspension of magnetic particles.

The mixture is incubated under appropriate conditions until a sufficient quantity of biological compartments are bound to the magnetic particles, usually between 1 minute and 10 minutes. The sample processing vessel is preferably closed in proper fashion, e.g. with a cap and/or a valve.

An important feature of the invention is the fact that the mixture in the sample processing vessel is shaken during incubation. The mixture can be shaken in intervals, or it can be shaking during the entire incubation period or only during certain periods. The mixture is shaken in order to sufficiently mix the biological compartments and the magnetic particles in the fluid, and especially to suspend or resuspend the beads and accelerate diffusion. This reduces the amount of time required to bind the biological compartments to the magnetic particles.

After the incubation step and after the compartments are bound to the magnetic particles, the biological compartments are removed from the surrounding fluid in the sample. An appropriate method of accomplishing this is to collect the magnetic particles and bound biological compartments by positioning a magnet near the sample processing vessel. This holds the magnetic particles with the biological compartments against the vessel wall, as is preferable. The beads are therefore usually separated on the inside wall of the sample processing vessel or a part thereof that is located below the surface of the sample fluid.

The fluid surrounding the biological compartments is then removed from the sample processing vessel. This is performed under conditions in which the magnetic particles remain against the vessel wall. The method used to remove the sample depends on the type of sample processing vessel used. The fluid can be removed via pipette, for instance. In a preferred construction, however, in which the sample processing vessel has an opening at the bottom from which the fluid can exit, the fluid is simply aspirated through this opening. This fluid removal method minimizes the mechanical stress placed on the magnetic particles and thereby prevents them from being removed from the vessel wall.

An especially important step is the resuspension of the magnetic particles that remain on the vessel wall in a second fluid that is added. To accomplish this, the magnet is moved away from the vessel so that it no longer holds the magnetic particles against the vessel wall. As described above, it is also possible to move the vessel away from the magnet. With regard for the invention described here, it has been demonstrated that simply removing the magnet is not enough to resuspend the magnetic particles in the solution if the vessel is not also shaken, and preferably simultaneously. This shaking motion is performed by the mechanical shaker (30). It causes the magnetic particles to be distributed evenly within the second fluid. This second fluid can be added to the sample processing vessel, e.g. via pipette, before or after the magnet is removed.

The procedure provided by this invention can also be used to further purify biological compartments. To accomplish this, a suspension of magnetic particles that bind with the biological compartments is positioned in a sample processing vessel in relation to a magnet in such a way that the magnetic particles with the biological compartments are held against the vessel wall. The fluid that contains the biological compartments is then removed from the vessel and the magnetic particles are resuspended in a second fluid—a wash fluid in this case—by moving the magnet away from the vessel so that the magnetic particles are no longer held against the vessel wall, while the vessel is shaken. This wash step can be repeated as needed until the biological compartments have reached a sufficient level of purity.

Another step of the procedure provided by this invention is the subsequent disintegration (lysis) of the biological compartments. Procedures for lysing biological compartments are known by the expert, as are the specific conditions for certain types of compartments,. e.g. cells. To lyse bacteria, for instance, a mixture of proteinase K is added to the biological compartments and incubated for the amount of time necessary to lyse or partially or completely decompose the cell walls and release the nucleic acids contained in the biological compartments. This procedure is preferably performed at temperatures above room temperature, and more preferably, at temperatures between 70 and 95° C. The mixture created when the cells are lysed is also referred to as the lysis mixture below. The incubation period is preferably from 5 to 20 minutes, and more preferably, from 10 to 15 minutes.

If the cells are lysed at room temperature or a temperature slightly above room temperature, it is especially preferable to then warm the lysis mixture to higher temperatures such as 70° C. or, if the samples are potentially infectious, to 95° C. The lysis can also be deactivated if it interferes with the subsequent steps.

The lysis mixture is then cooled under conditions that depend on the purpose for which the procedure provided by this invention is performed. If the nucleic acids are isolated on a solid phase, conditions are selected under which the nucleic acids can bind to the solid phase. A suitable procedure for binding nucleic acids is the incubation of released nucleic acids with glass surfaces in the presence of chaotropic salts. A procedure of this nature is described in EP-A-0 389 063, for instance. In this procedure, the nucleic acids are bound non-specifically to the glass surface, while other components of the biological compartments and the lysis reagent are not bound to the glass surface, or are only bound insignificantly. The fluid that contains the remaining components is then preferably removed from the sample processing vessel, e.g. via aspiration, while the glass surface can remain in the sample processing vessel with the nudeic acids bound to it. In a preferred construction, a solid phase in the form of a glass fiber fleece is placed in the sample processing vessel and incubated with the mixture. In this procedure, the nucleic acids are immobilized on the glass fibers and can simply be removed from the sample processing vessel with the glass fiber fleece.

If the nucleic acids will be detected after their release, they are hybridized with a probe. This probe, as described above, is a molecule that has a base sequence that is complementary to the nucleic acid to be detected or a part thereof. In a preferred case, this is an oligonucleotide labelled with a group to be detected. The reaction mixture is therefore cooled under conditions in which the nucleic acids to be detected hybridize with the nudeic acid probe. These temperatures are known by the expert. In another construction of the procedure for detection of nucleic acids, the nucleic acids to be detected hybridize with a nucleic acid probe bound to a solid phase. In this procedure, the probe can be used on any solid phase, such as microtiter plate cavities or the inside wall of the sample processing vessel, as long as it is separated only from the rest of the reaction mixture. Procedures for immobilizing nucleic acid probes, especially "capture" probes, are known by the expert, e.g. from EP-A-0 523 557.

After the mixture is cooled, the nucleic acids to be isolated or detected are then separated from the surrounding fluid that may still contain remains of the lysis mixture and reagents used to bind the nucleic acids to a solid phase. Depending on the type of solid phase used, the solid phase can be filtered or removed from the sample processing vessel, or the fluid can be removed from the sample processing vessel by pipette.

The bound nucleic acids can then be unbound from the solid phase, detected directly in common procedures for detecting nucleic acid sequences known by the expert, or labelled.

Version B

In the initial step, the sample is pipetted into a sample processing vessel along with lysing reagent and glass-magnetic particles (beads) that can bind with the nucleic acids contained in the biological compartments. The sample processing vessel is then closed and shaken. It is necessary for the sample, lysis reagent and glass-magnetic particles to be placed in the sample processing vessel. Neither the method by which they are placed in the vessel nor the sequence in which this takes place is especially significant for the procedure provided by this invention. Preferably, however, the glass-magnetic particles are pipetted into the sample processing vessel in a suspension with a known concentration of glass-magnetic particles. The sample is pipetted into the sample processing vessel either before or after the suspension of glass-magnetic particles. It is essential that the sample, glass-magnetic particles and lysis reagent are shaken until mixed thoroughly.

Another step of the procedure provided by this invention is the subsequent disintegration (lysis) of the biological compartments. Procedures for lysing biological compartments are known by the expert, as are the specific conditions for certain types of compartments, e.g. cells. To lyse bacteria, for instance, a mixture of proteinase K is added to the biological compartments and incubated for the amount of time necessary to lyse or partially or completely decompose the cell walls and release the nucleic acids contained in the biological compartments. This procedure is preferably performed at temperatures above room temperature, and more preferably, at temperatures between 70 and 95° C. The mixture created when the cells are lysed is also called the lysis mixture below. The incubation period is preferably from 5 to 20 minutes, and more preferably, from 10 to 15 minutes.

If the cells are lysed at room temperature or a temperature slightly above room temperature, it is especially preferable to then warm the lysis mixture to higher temperatures such as 70° C. or, if the samples are potentially infectious, to 95° C. The lysis can also be deactivated if it interferes with the subsequent steps.

An important feature of the invention is the fact that the mixture in the sample processing vessel is shaken during incubation. The mixture can be shaken in intervals, or it can be shaking during the entire incubation period or only during certain periods. The mixture is shaken in order to sufficiently mix the biological compartments and the magnetic particles in the fluid, and especially to suspend or resuspend the beads and accelerate diffusion. This reduces the amount of time required to bind the biological compartments to the magnetic particles.

The lysis mixture is then cooled under conditions that depend on the purpose for which the procedure provided by this invention is performed. The nucleic acids released from the biological compartment should now bind non-specifically to the surface of the glass-magnetic particles. To improve the binding characteristics, i-propanol or ethanol—depending on the type of biological compartment involved—is added to the lysis mixture after lysis. The sample processing vessel is then shaken to mix the mixture further. The nucleic acids are now bound non-specifically to the surface of the solid phase. Other components of the biological compartment and lysis reagents do not adsorb to the glass surface, or only insignficant components adsorb to the glass surface.

After the solid phase binding step is complete, the magnetic fields are activated in order to deposit the glass-magnetic pigment with the bound nucleic acids on the inside surface of the sample processing vessel. The remaining fluid is then removed from the vessel. In a preferred construction, however, in which the sample processing vessel has an opening at the bottom from which the fluid can exit, the fluid is simply aspirated through this opening. This fluid removal method minimizes the mechanical stress placed on the magnetic particles and thereby prevents them from being removed from the vessel wall.

In a subsequent step, the glass-magnetic particles are resuspended in a wash fluid. To accomplish this, the magnet is moved away from the vessel so that it no longer holds the magnetic particles against the vessel wall. As described above, it is also possible to move the vessel away from the magnet. With regard for the invention described here, it has been demonstrated that simply removing the magnet is not enough to resuspend the magnetic particles in the solution if the vessel is not also shaken, and preferably simultaneously. This shaking motion is performed by the mechanical shaker (30) and causes the magnetic particles to be distributed evenly within the second fluid. This second fluid can be added to the sample processing vessel, e.g. via pipette, before or after the magnet is removed. This wash step can be repeated as needed until the biological compartments have reached a sufficient level of purity.

The bound nucleic acids can then be unbound from the solid phase, detected directly in common procedures for detecting nucleic acid sequences known by the expert, or labelled.

The procedure provided by this invention is therefore based on a combination of steps that make use of a receptacle (10) for holding one or more sample processing vessels, a thermostat unit (20) to maintain the sample processing vessels and the fluid in them at a constant temperature, a mechanical shaker (3) to shake the sample processing vessels, and a unit (40) for separating and depositing the magnetic particles on a wall of each sample processing vessel using magnetic force. Surprisingly, these steps and units can be combined into a single reaction block. A reaction block in this case refers to a device that comprises all or some of the units 10, 20, 30 and 40 coupled in coordinated fashion. This invention enables a process to be performed in one instrument that used to require numerous manual preparation steps. The reaction blocks provided by this invention have been demonstrated to be especially effective. Procedures for the release and isolation of nucleic acids can now be performed more quickly with this system than before. The system also makes it possible to leave the nucleic acids in the vessel during the steps described. This represents a considerable advance over the state of the art in terms of time savings and avoiding contamination. Suspensions were usually cooled previously by manually removing a sample processing vessel from the instrument and immersing it in a cooling bath. This procedure has been demonstrated to be insufficient for the future of routine diagnostic testing procedures.

Figure 3:
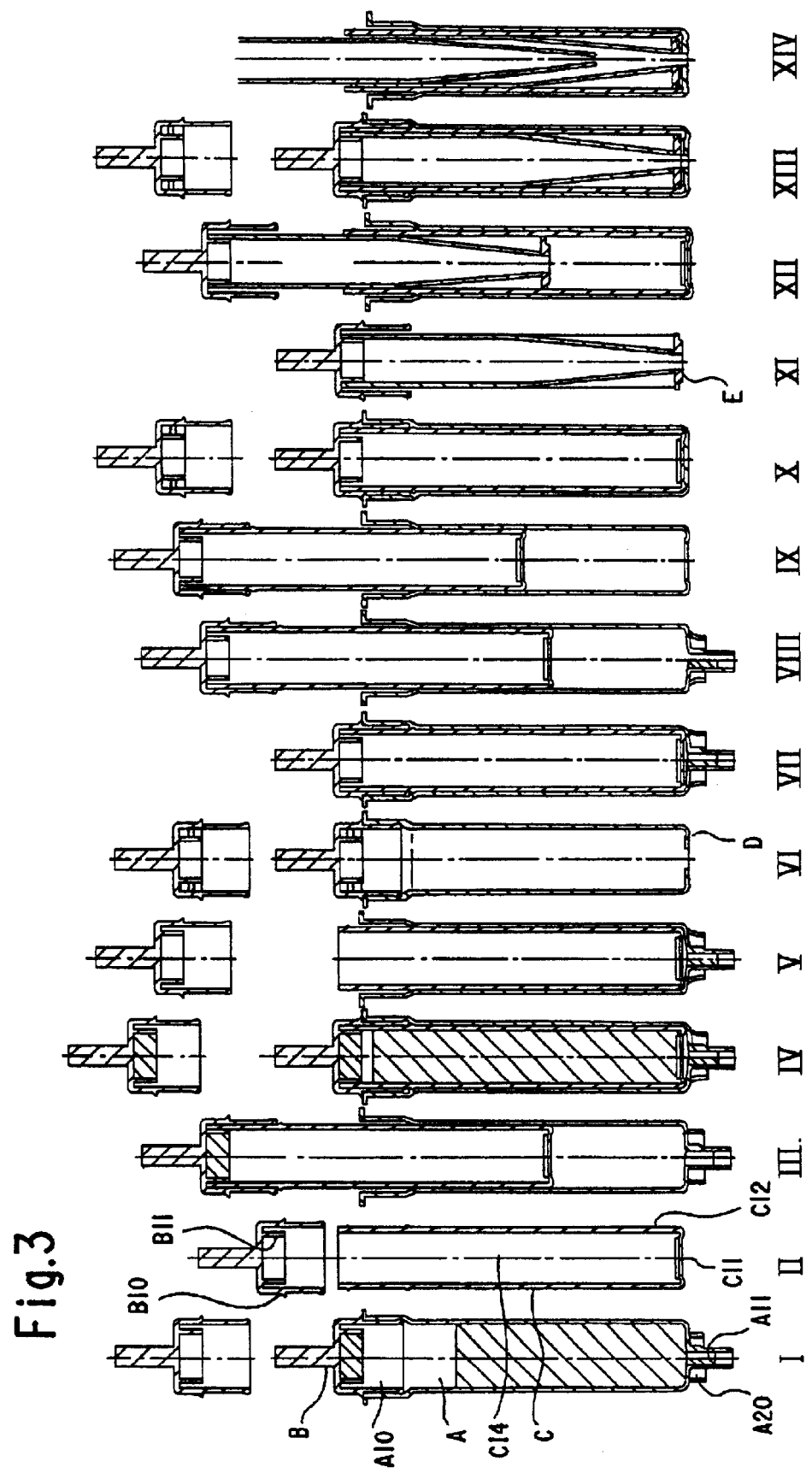
FIG. 3 shows a procedure for isolating nucleic acids provided in the invention.

FIG. 3 shows a procedure for isolating nucleic acids provided by this invention. This figure is referred to in the procedure described in the example below. The sample vessel is located in a receptacle in unit 10. The sample vessel preferably has a stem (A20) that is molded to fit within the receptacle (e.g. it is conical in shape). The vessels shown in cross-section can be made simply from polypropylene using injection molding techniques.

A main advantage of the invention is the fact that the system can be adapted to a large extent for use with different sizes of magnetic particles. It is relatively flexible and can be used with the most diverse procedures.

The object of the invention is explained in greater detail using the example below:

EXAMPLE 1

The basic principles of the procedure provided by this invention are known by experts in nucleic acid diagnostics. Any technical details not listed below can be found in "Molecular Cloning" by J. Sambrook et al., CSH 1989.

A particular construction of the procedure for processing sample solutions containing nucleic acids provided by this invention comprises the following working steps (see FIG. 3). In the initial step (I), a sample fluid containing cells is incubated in a sample vessel (A) with a material to which the cells bind and from which nucleic acids will be extracted. This material can have binding characteristics specific for cell surfaces, e.g. antibodies against surface antigens are immobilized on an absorber material (A16, not shown). Or, the material can have filter characteristics (A15, not shown) that retain the cells when the fluid flows through the material, e.g. as it is being removed from the sample vessel. Conditions for immobilizing cells on surfaces are known by the expert, e g. from "Methods in Enzymology", Vol 171, Biomembranes/Part R Transport Theory: Cell and Model Membranes, edited by Sidney Fleischer, Becca Fleischer, Department of Molecular Biology, Vanderbilt University, Nashville, Tenn., pages 444 ff or 581 ff.

During incubation, the sample vessel is preferably closed with a cap (B) to ensure active and passive protection from contamination.

In a subsequent step, the fluid is removed from the sample vessel while the cells containing the nucleic acids to be isolated remain in the sample vessel bound to the material. Since the cell-binding material is a particular material, retention is achieved by the fact that the material is magnetic (manufactured by Dynal, Oslo, Norway), and the magnet is moved towards the sample vessel from the outside. The fluid can be aspirated through the outlet (A 11) by creating a slight vacuum. To accomplish this, a valve is built into the outlet that opens when a vacuum is created.

One or more wash steps are provided in order to remove remaining sample components from the cells that may cause interference. In these steps, a wash fluid is added to the sample vessel in which any contaminants present dissolve but which does not have a negative effect on the cells binding to the surface of the cell-binding material. Wash solutions of this nature are known by the expert, e.g. from cell separation protocols or appropriate purification kit protocols for nucleic acids. They basically depend on the way the cells are bound to the material.

Once the last wash solution is aspirated from the sample vessel (A), the purified, enriched cells are brought in contact with an appropriate lysis fluid to release the nucleic acids from the cells. The reagents of this lysis solution basically depend on the type of cells immobilized (Rolfs et al.: P Clinical Diagnostics and Research, Springer Publishers, 1992, pg. 84 fif). If the cells are bacterial, the lysis solution preferably contains proteinase K to decompose the cell wall. If desired, the lysis can be encouraged with heating or cooling steps or mixing the reaction mixture by shaking the sample vessel. When lysis is complete, the nucleic acids to be isolated are freely available in the solution.

The reaction vessel Is also preferably closed with a cap during the lysis step, in order to prevent contamination from the environment When lysis is complete, the cap is removed, preferably by using an appropriate mechanical device. A moulded article (C) is then inserted into the sample vessel that contains a mixture of cellular decomposition products and nucleic acids, the external contour of which (C 12) is coordinated with the internal contour (A 17) of the sample vessel. This moulded article is hollow and closed with a filter (C 11) (porous matrix) on the end situated towards the sample vessel and the reaction mixture. The moulded article (C) is preferably inserted using a component (B 10) that is suitable for closing the sample vessel. In this case, the moulded article is held by the cap (II) and inserted into the sample vessel when it is closed. During this process, the reaction mixture also enters the hollow space (C 14) of the moulded article through the filter (C 11) (IV). The filter can prevent large particles from entering the hollow space and, due to its nucleic acid-binding characteristics, it binds nucleic acids even as the reaction mixture passes through. A filter material containing glass fibers is selected for use in this case.

In a subsequent step, the remaining lysis reaction mixture is removed from the device formed by A and C by aspirating it through the outlet (A11) in the sample vessel. This procedure also removes the solution that entered the hollow body (C14) of the moulded article, leaving as little filter residue in the filter as possible. The cap (B) is then removed, but the moulded article (C) remains in the sample vessel.

At the same time or immediately thereafter, an elution vessel (D) is prepared to receive the moulded article (C) (either in the system provided by this invention or outside of it). If this vessel has a cap, it is removed (VI). Preferably, an elution solution is added to the elution vessel before the moulded article (C) is inserted into the elution vessel (D), e.g. using a pipette. The composition of the elution solution is based on the type of nucleic acid binding with the material in the filter (C). It contains reagents that cause the Immobilized nucleic acids to elute, e.g. dissolve, from the material. The cap (B) that originally covered the elution vessel is placed on the sample vessel (A) with the moulded article (C) (VII).

To remove the moulded article (C) from the sample vessel (A), the moulded article (C) is removed along with the cap (B) (VIII). The combination of cap and moulded article is then Inserted in the elution vessel (IX). The moulded article (C) preferably contains a means (C13, not shown) for fixing the moulded article in the elution vessel (D) that ensures that the moulded article can only be removed from the vessel (D) if the moulded article (C) or vessel (D) is destroyed, or a force is used that is stronger than the force used to loosen the cap (B) from the moulded article (C). It is not intended for the moulded article to be removed from the elution vessel.

While the moulded article (C) enters the elution vessel, the elution solution in the vessel enters the filter (C 11) and loosens the immobilized nucleic acids from the solid matrix. Depending on the quantity of elution solution in the vessel, the filter is either just saturated with the elution solution, or the elution solution—and the redissolved nucleic acids—enter the hollow space (C 14). To ensure that the nucleic acids are eluted as completely as possible, the inner contour of the elution vessel should fit as tightly against the external contour of the moulded article as possible.

In a subsequent step, the cap (B) is removed from the combination of moulded article (C) and elution vessel (D) (X). It is used to pick up a stamp (E) XI) and insert it into the hollow space of the moulded article (C) (XII). The cap grips the stamp (E) from inside. The stamp is pressed against the filter (C 11) with such force that fluid from the filter enters an internal space in the stamp through an opening on the pressing surface. This procedure is especially effective if the external contour of the pressing surface is coordinated with the inner contour of the moulded article (C), at least in the area intended for pressing. The stamp (E) can preferably be fixed in this position, e.g. by snapping it into place. Since the cap closes the device with this construction relatively tightly, the solution containing nucleic acids can be stored in this device.

To remove a desired quantity of nucleic acid solution, the cap can be removed (XIII) and the desired quantity of solution can be removed through an opening in the internal space of the stamp, e.g. by pipette (XIV). The cap can then be placed back on the tube.

The sequence of steps of the procedure described is provided below.

| Instrument | Operator |
| --- | --- |
| automated (program controlled) | manual |
| incubate | pipette |
| aspirate | place tubes, glass fleece insert and back-up container on the instrument |
| separate (magnetic solid phase) | |
| mix/resuspend | |

Manual working steps are shown in bold. Non-manual working steps or partial sequences are called up by pressing a key, for instance.

In the table below, the sample vessel A is called a tube, the elution vessel D is referred to as the back-up vessel, the moulded article C is referred to as the glass fleece insert, and the stamp E is called the press stamp.

| Step # | Action | Time(s) |
|---|---|---|
| 1 | Place tube #1–16 in the reaction module. | |
| 2 | Pipette receptor (50–100 µl) and SA beads (50–100 µl in tubes #1–16 | |
| 3 | Pipette sample (1000 µl) in tubes #1–16 | |
| 4 | Close tubes with cap (16 each) | |
| 5 | Mix. Frequency = 30 Hz (parallel) | 30 s |
| 6 | Incubation. 9 = 4° C. After incubation 9 = RT (parallel) | 300–1200 s |
| 6* | Mix (if necessary) during incubation | |
| 7 | Magnet ACTIVATED (in parallel) | 5 s |
| 8 | Aspirate waste (sequentially, 5 s) | 80 s |
| 9 | Magnet DEACTIVATED (in parallel) | 5 s |
| 10 | Open the cap on the tubes (16 each) | |
| 11 | 1st wash step: Pipette 500–1000 µl wash solution (low molecular weight salt) into tubes #1–16 | |
| 12 | Resuspend. Frequency = 30 Hz (in parallel) | 5 s |
| 13 | Magnet ACTIVATED (in parallel) | 5 s |
| 14 | Aspirate waste (sequentially, 5 s) | 80 s |
| 15 | Magnet DEACTIVATED (in parallel) | 5 s |
| 16 | 2nd wash step: Pipette 500–1000 µl wash solution (low molecular weight salt) into tubes #1–16 | |
| 17 | Resuspend. Frequency = 30 Hz (in parallel) | 5 s |
| 18 | Magnet ACTIVATED (in parallel) | 5 s |
| 19 | Aspirate waste (sequentially, 5 s) | 80 s |
| 20 | Magnet DEACTIVATED (in parallel) | 5 s |
| 20.1 | 3rd wash step (optional): Pipette 500–1000 µl wash solution (low molecular weight salt) into tubes #1–16 | |
| 20.2 | Resuspend. Frequency = 30 Hz (in parallel) | 5 s |
| 20.3 | Magnet ACTIVATED (in parallel) | 5 s |
| 20.4 | Aspirate waste (sequentially, 5 s) | 80 s |
| 20.5 | Magnet DEACTIVATED (in parallel) | 5 s |
| 21 | Pipette lysis mix, reagent 1 + 2 (400 µl guanidinium hydrochloride or guanidinium rhodanide and proteinase K (25 µl) in tubes #1–16 | |
| 22 | Close the tubes with the caps (16 each) | |
| 23 | Resuspend. Frequency = 30 Hz (in parallel) | 5 s |
| 24 | Incubation: 9 = 70° C. [Optional: Incubation: 9 = 95° C. with potentially infectious samples] | 600 s 900 s |
| 25 | Incubation: 9 = RT | 300 s |
| 26 | Open the caps on the tubes (16 each) | |
| 27 | Pipette 200 µl ethanol (isopropanol) into tubes #1–16 | |
| 28 | Close the caps on the tubes (16 each) | |
| 29 | Mix. Frequency = 30 Hz (in parallel) | |
| 30 | Open the caps on the tubes (16 each) | |
| 31 | Place glass fleece insert in tube #1 into tubes #1–16 | |
| 32 | Aspirate waste (sequentially, 5 s) | 80 s |
| 33 | Pipette 500 µl wash solution (chaotropic salt/ethanol) into tubes #1–16 | |
| 34 | Aspirate waste (sequentially, 5 s) | 80 s |
| 35 | Pipette 500 µl wash solution (chaotropic salt/ethanol) into tubes #1–16 | |
| 36 | Aspirate waste (sequentially, 5 s) | 80 s |
| 37 | Place back-up vessel on the instrument (#1–16) | |
| 38 | Pipette elution volume into the back-up vessel (100–200 µl) into tubes #1–16 | |
| 39 | Transfer glass fleece insert from tube #1 to the back-up vessel (#1–16) | |
| 40 | Insert press stamp (#1–16) into the back-up vessel - Elution | |
| 41 | Close the back-up vessel (16 caps) | |
| 42 | Remove tubes #1–16 from the RM - waste | |

If desired, the suction tubes and the cavities can be rinsed and, therefore, cleaned, with a cleaning fluid (before or after the procedure is performed and after the sample vessels have been removed).

Another construction of a system for the release and isolation of nucleic acids is shown in FIGS. 4 through 8.

Figure 4:
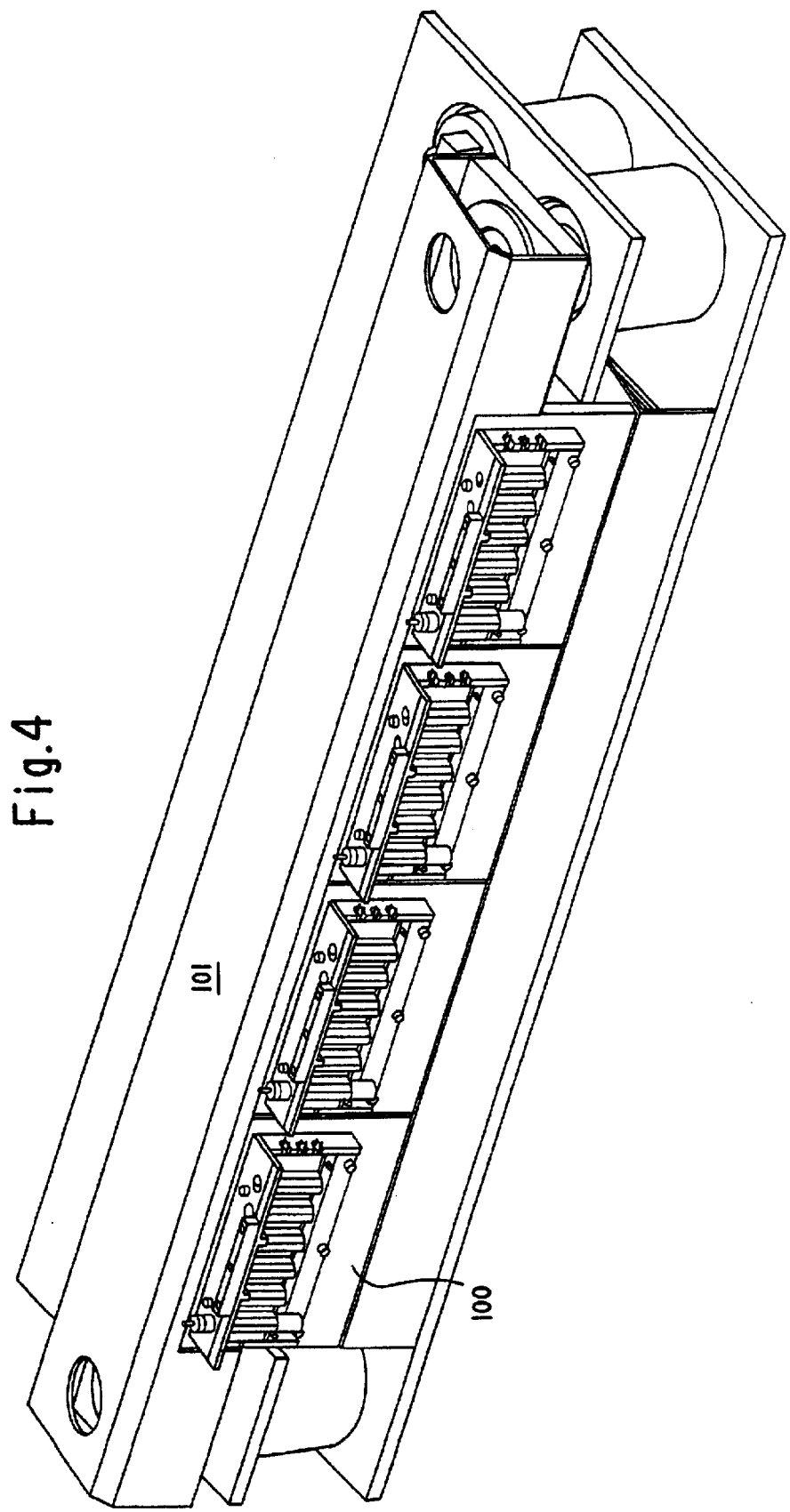
FIG. 4–8 show another construction of a system for the release and isolation of nucleic acids in accordance with the invention.
Figure 5:
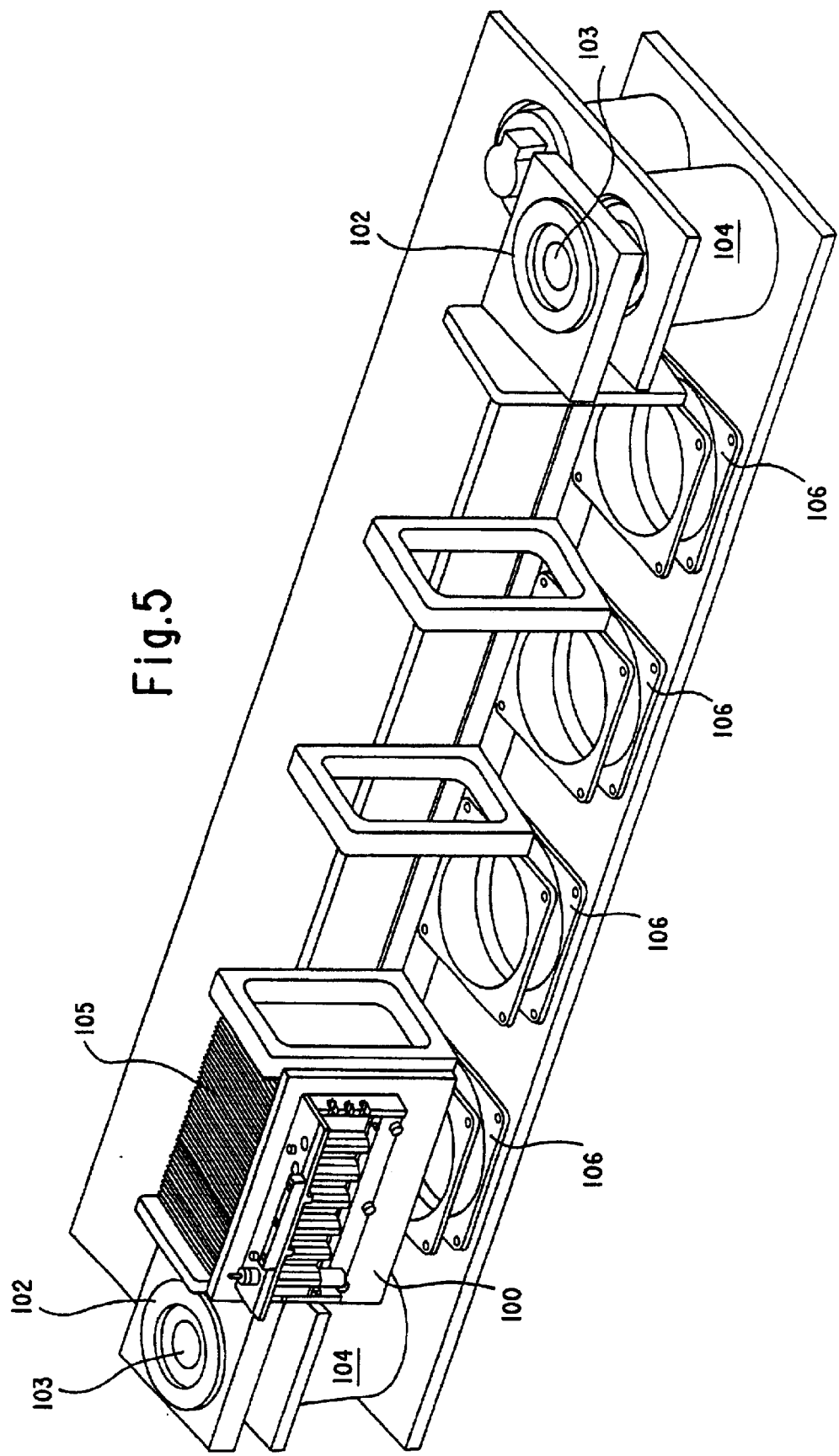

FIG. 4: Perspective drawing of the system
FIG. 5: Phantom drawing of the system
FIG. 6: Receptacle for sample processing vessels
FIG. 7: Cross-section through a receptacle for a sample vessel
FIG. 8: Pushing device with magnets The system shown in FIG. 4 has 4 receptacles (100) for sample vessels. The receptacles (100) are fixed to a carrier (101). Moving the carrier (101) moves and shakes the 4 receptacles (110) in unison. The phantom drawing (FIG. 5) illustrates in greater detail how the movement of the carrier (101) takes place. The carrier has a circular recess (102) on each of its 2 ends in which a rod (103) is situated. The rod (103) is situated on the axis of a motor (104) in an eccentric position. When the motor axis turns, therefore, the carrier is shifted along a plane. The phantom drawing (FIG. 5) also illustrates clearly that the receptacle (100) has cooling fins (105). A stream of air is blown through the cooling ribs by means of ventilating fans (106) located on the base of the system to cool the system.

Figure 6:
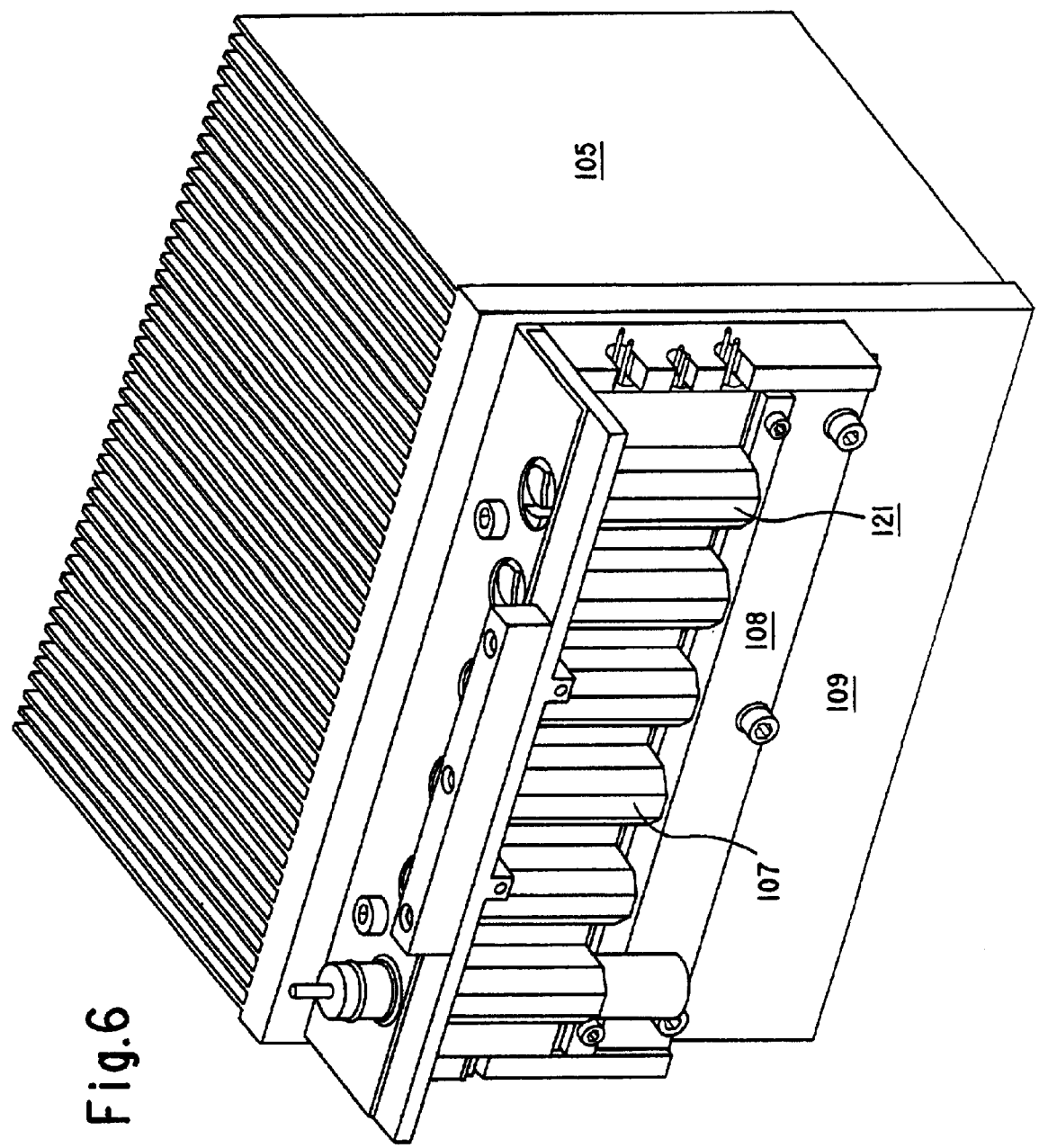

A receptacle (100) is shown in greater detail in FIG. 6. The receptacle has 6 separate cavities (107) to receive sample processing vessels. The cavities (107) are connected with the peltier element (109) by means of a framework (108) in a thermally conductive fashion. The peltier element, in turn, is connected with the cooling fins (105). The frame (108) contains temperature sensors and a resistance heating device to warm the cavities. The frame (108) is mounted on a peltier element (109) that exchanges heat with the cooling fins (105). The sample processing vessels are warmed by the heating elements located in the frame. The cavities (107) are cooled by the peltier element (109) in order to cool the sample processing vessels. The heat emitted by the peltier element on the opposite side is eliminated through the cooling fins (105).

Figure 7:
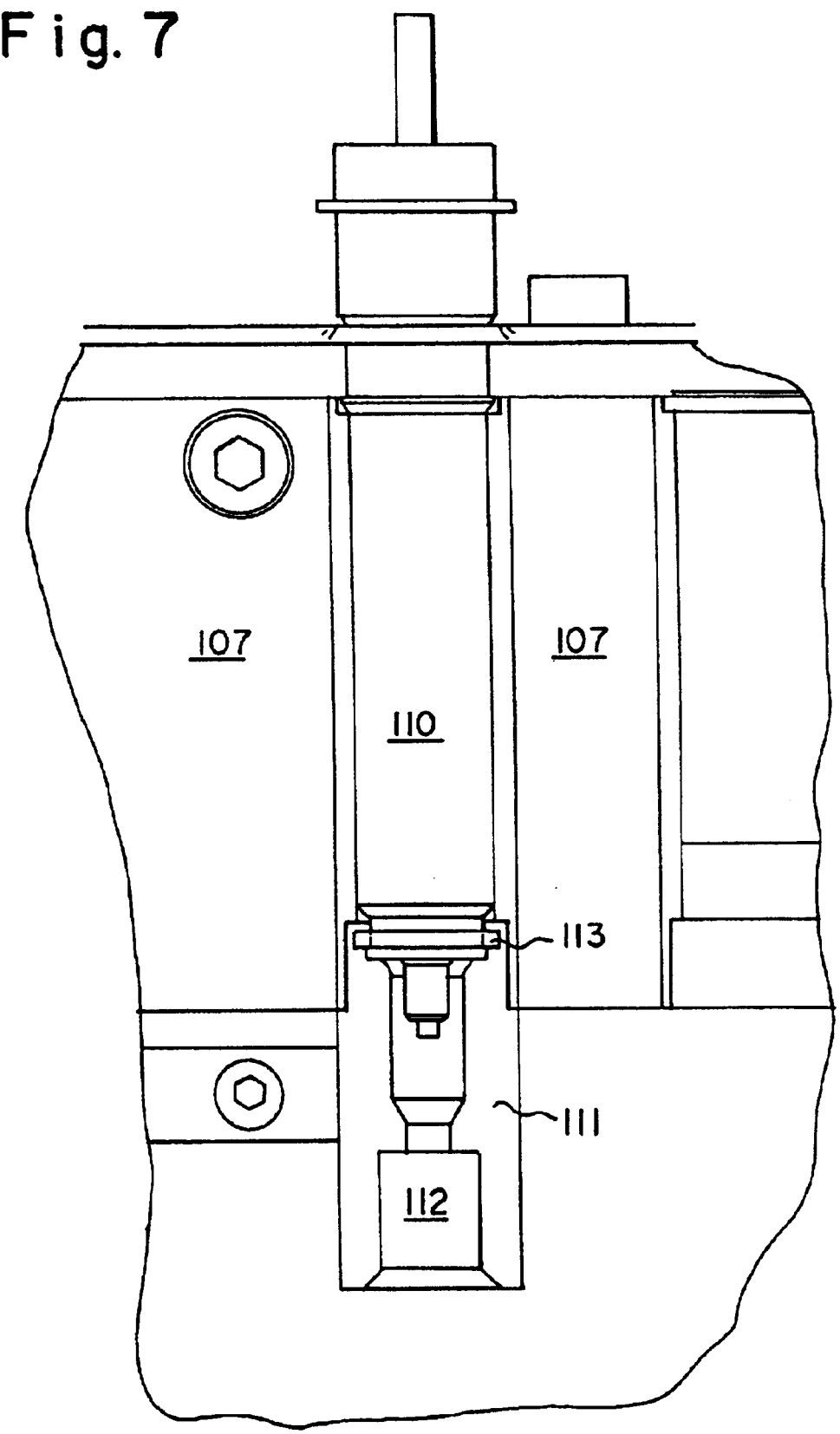

FIG. 7 shows a cross-section of one cavity (107). The cavity consists of a cylindrical space in which a sample vessel (110) is located. The sample vessel and cylindrical space are designed in such a way that the walls touch each other, to promote efficient heat transfer. Preferably, the sample vessel and cavity are both slightly conical, i.e. they taper towards the bottom, so that a snug fit is achieved. The conicity is preferably between 0.5 and 1°. An insert is situated in the lower portion of the cavity that has a recess (112) on its underside into which a hose connection can be screwed. On the upper end, the insert (112) has an opening into which the tapered tip of a sample vessel (110) can be inserted. To achieve a tight connection between this opening and the tapered tip of the sample vessel, a sealing ring (113) in the shape of an O-ring that surrounds the tapered tip of the sample vessel is located in this position. To remove fluid from the sample vessel (110), a vacuum is created in the sample vessel (110) by means of a tube that is connected to the opening (112).

When the system is operated as provided by this invention, a magnetic field can be applied to the sample vessels (110) while they are situated in the cavities (107), to hold magnetic particles. The magnet assembly shown in FIG. 8 is moved towards the cavities (107) for this purpose.

Figure 8:
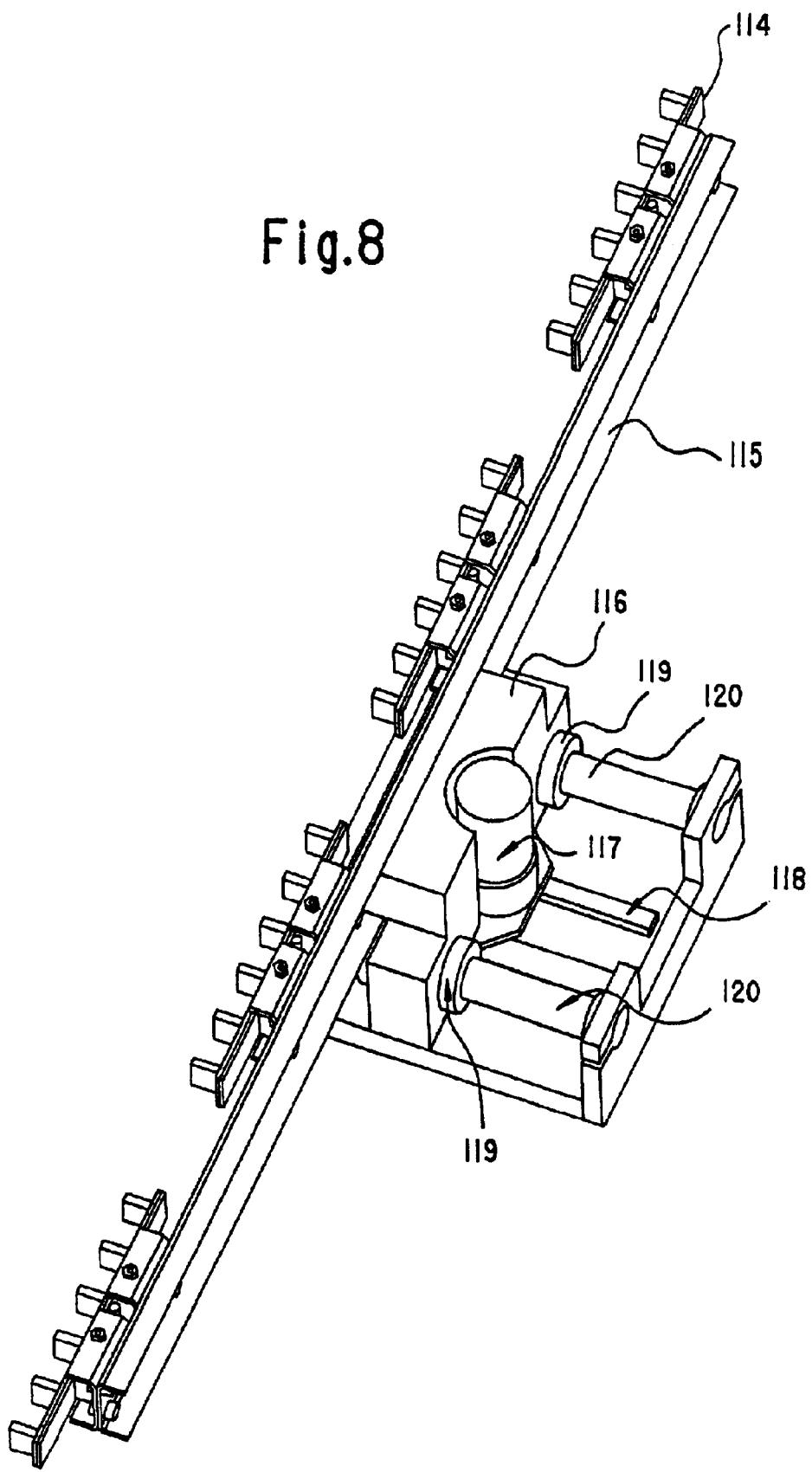

FIG. 8 shows a moveable assembly of 4×6 magnets (114), corresponding to the 4 receptacles (110) with 6 cavities (107) each. The assembly shown in FIG. 8 has a rail (115) on which 4 units of 6 magnets each are mounted. The rail (115) is fixed to the carrier (116) which, in turn, holds a motor (117). A gearwheel (not shown) is mounted to the axis of the motor that grips the teeth (not shown) of a gear rack (118). The carrier (116) is arranged on cylinders (120) in such a fashion that it can be pushed along by linear ball bearings (119). In the position in which magnetic particles are deposited, the front surfaces of the magnets (114) are located directly against the flat sides (121) of the cavities (107). To move the magnets away from the cavities, the motor (117) is activated and the carrier, including the rail (115) is moved in linear fashion.

Reference Drawing List

A Sample Vessel
  10 Inlet
  11 Outlet
  17 Internal contour
  19 External contour
  20 Stem base
  22 Element to which additional functional elements can be attached
B Cap
  10 Component for closing sample vessel A
  11 Component for gripping the moulded article C
C Moulded Article
  11 Porous matrix
  12 External contour
  13 Means for fixing the moulded article in the elution vessel
  14 Hollow body
  15 Means for attaching a cap
  16 Internal contour
  17 Means for fixing a stamp E into position, all the way around
  18 Stem base, can be broken off
  19 Edge
D Elution Vessel
  12 Snap-in notch
E Stamp
  10 Pressing surface
  11 External contour
  12 Internal space
  13 Openings in the pressing surface
  14 Opening for removing contents
  15 Seal
  16 Snap-in ring
  17 Recess Instrument 1 Frame
10 Receptacle for sample vessels
11 Vibration absorber
12 Cavity
13 Base
14 Inlet to heat and cool A
20 Thermostat unit to maintain sample vessels at a constant temperature
21 Duct for cooling/heating
30 Mechanical shaker for sample vessels
40 Separator for separating magnetic particles using magnetic force
41 Axis for turning magnet segments
42 Magnet segments
50 Vacuum pump/pump unit
51 (Vacuum) tube
100 Receptacle for sample vessels
101 Carrier
102 Circular recess
103 Rod
104 Motor
105 Cooling fins
106 Ventilator
107 Cavity
108 Frame
109 Peltier element
110 Sample vessel
111 Insert
112 Opening
113 Sealing ring
114 Magnet
115 Rail
116 Carrier
117 Motor
118 Gear rod
119 Linear bail bearing
120 Cylinder

What is claimed is:

1. A method of isolating nucleic acids from biological compartments of a fluid sample comprising the steps of:
   incubating the sample in a sample processing vessel with magnetic particles which magnetic particles are capable of binding with the biological compartments;
   positioning at least one magnet towards the sample processing vessel to hold the magnetic particles against an inside wall of the sample processing vessel by magnetic force;
   removing the remaining fluid, from which the biological compartments have been separated, from the sample processing vessel;
   introducing a second fluid into the sample processing vessel;
   resuspending the magnetic particles in the second fluid by eliminating the magnetic force which held the magnetic particles against the inside wall of the sample processing vessel, and shaking the sample processing vessel in the absence of the magnetic force;
   thereafter lysing the biological compartments to form a lysis mixture; and
   isolating the nucleic acids from the lysis mixture.

2. The method of claim 1, wherein essentially all of the magnetic particles have a diameter of 2.8 $\mu$m to 200 $\mu$m.

3. The method of claim 2, wherein the average magnetic particle size diameter is about 10 $\mu$m to 15 $\mu$m.

4. The method of claim 1, wherein the isolation step comprises immobilizing the nucleic acids on the magnetic particles.

5. The method of claim 1, wherein the nucleic acids to be isolated are transferred to another vessel which is configured to receive a pipette.

6. The method of claim 1, wherein the magnetic force is eliminated by separating by a sufficient distance the at least one magnet from the outside wall of the sample processing vessel.

7. The method of claim 1, wherein the magnetic force is eliminated by positioning a $\mu$-metal between the vessel and the at least one magnet.

8. The method of claim 1, wherein each magnet has a mass of about 0.5 g to about 5 g.

9. The method of claim 1, wherein each magnet has a mass of about 1 g to about 4 g.

10. The method of claim 1, wherein the processing vessel containing the sample is shaken during at least a portion of the incubation step to facilitate binding.

11. The method of claim 1, wherein the magnetic force is eliminated and the sample processing vessel is shaken simultaneously.

12. The method of claim 1, wherein the steps of positioning at least one magnet near an outside wall of the sample processing vessel such that it holds the magnetic particles against an inside wall of the sample processing vessel, removing the remaining fluid, from which the biological compartments have been separated, from the sample processing vessel, and resuspending the magnetic particles in a second fluid by eliminating the magnetic force which held the magnetic particles against the inside wall of the sample processing vessel, and shaking the sample processing vessel, are repeated until the biological compartments have reached a desired level of purity.

13. The method of claim 1, wherein the fluid sample is a body fluid.

14. The method of claim 1, wherein the fluid is blood, saliva or urine.

15. The method of claim 1, wherein the nucleic acids are isolated by warming the lysis mixture for a sufficient period of time so as to lyse or partially or completely decompose cell walls of the biological compartments and release the nucleic acids contained in the biological compartments, and cooling the lysis mixture under conditions that make it possible to isolate or hybridize the nucleic acids to be isolated or detected.

16. The method of claim 15, wherein the lysis mixture is warmed to a temperature above room temperature.

17. The method of claim 16, wherein the lysis mixture is warmed to a temperature of about 70° to about 95 ° C.

18. The method of claim 1, wherein the nucleic acids are present in the sample reaction vessel throughout the removing, resuspending and lysing steps.

19. The method of claim 1, wherein the removing, resuspending and lysing steps take place within a reaction block.

20. The method of claim 19, wherein the reaction vessels remain in the reaction block during the removing, resuspending, and lysing steps.

21. The method of claim 1, further comprising the step of detecting the nucleic acids.

22. A method of isolating nudeic acids from biological compartments of a fluid sample comprising the steps of:

incubating the sample in a sample processing vessel with magnetic particles which magnetic particles are capable of binding with the biological compartments;

positioning at least one magnet towards the sample processing vessel to hold the magnetic particles against an inside wall of the sample processing vessel by magnetic force;

removing the remaining fluid, from which the biological compartments have been separated, from the sample processing vessel;

introducing a second fluid into the sample processing vessel;

resuspending the magnetic particles in the second fluid by eliminating the magnetic force which held the magnetic particles against the Inside wall of the sample processing vessel, and shaking the sample processing vessel in the absence of the magnetic force;

thereafter lysing the biological compartments to form a lysis mixture; and warming the lysis mixture; and cooling the lysis mixture under conditions that make it possible to isolate or hybridize the nucleic acids to be isolated or detected.

23. The method of claim 22, further comprising shaking the sample processing vessel during the incubating to facilitate the binding of magnetic particles to the biological compartments.

24. The method of claim 1, wherein the sample processing vessel has an opening at the bottom from which fluid can exit.

* * * * *